United States Patent
Kasielke et al.

(10) Patent No.: US 9,579,036 B2
(45) Date of Patent: Feb. 28, 2017

(54) SENSOR FOR MONITORING A CONDITION OF A PATIENT

(71) Applicants: Roche Diabetes Care, Inc., Indianapolis, IN (US); Roche Diagnostics International AG, Burgdorf (CH)

(72) Inventors: Joachim Kasielke, Bruhl Deutschland (DE); Ulrich Haueter, Grosshochstetten (CH); Ulrike Kamecke, Mannheim (DE); Christian Hof, Bern (CH); Matthew Reynolds, Durham, NC (US); Timon Kasielke, Karlsruhe (DE); Steven Gray, Charlotte, NC (US); Harvey B Buck, Indianapolis, IN (US); Michael Lukin, Hertfordshire (GB); Fritz Hindelang, Carlsberg (DE)

(73) Assignees: Roche Diabetes Care, Inc., Indianapolis, IN (US); Roche Diagnostics International AG (CH)

( * ) Notice: Subject to any disclaimer, the term of this patent is extended or adjusted under 35 U.S.C. 154(b) by 862 days.

(21) Appl. No.: 13/739,189

(22) Filed: Jan. 11, 2013

(65) Prior Publication Data

US 2014/0066737 A1 Mar. 6, 2014

Related U.S. Application Data

(62) Division of application No. 11/742,998, filed on May 1, 2007, now abandoned.

(51) Int. Cl.
*A61B 5/05* (2006.01)
*A61B 5/1486* (2006.01)
(Continued)

(52) U.S. Cl.
CPC ............ *A61B 5/05* (2013.01); *A61B 5/14865* (2013.01); *A61B 5/746* (2013.01); *A61B 5/0002* (2013.01); *H05K 1/147* (2013.01); *H05K 3/323* (2013.01)

(58) Field of Classification Search
CPC ............ A61B 2562/164; A61B 5/1411; A61B 5/0002; A61B 2562/02; A61B 2562/00
See application file for complete search history.

(56) References Cited

U.S. PATENT DOCUMENTS 6,175,752 B1 * 1/2001 Say ..................... A61M 5/1723
128/903
6,248,067 B1 6/2001 Causey, III et al.
(Continued)

FOREIGN PATENT DOCUMENTS

EP   1733676 A1   12/2006
EP   1759726      3/2007

OTHER PUBLICATIONS

PCT International Preliminary Report on Patentability relating to corresponding International Application No. PCT/EP2008/003505 dated Feb. 7, 2009 (7 pages).
(Continued)

*Primary Examiner* — Jacqueline Cheng
*Assistant Examiner* — Angeline Premraj
(74) *Attorney, Agent, or Firm* — Barnes & Thornburg LLP

(57) ABSTRACT

A sensor may include a substrate having a sensing portion defining a sensor thereon and a circuit mounting portion defining at least one electrically conductive pad that is electrically connected to the sensor. The sensor may be configured to produce a signal indicative of a condition of the patient. An anisotropic medium may be disposed on the circuit mounting portion and may be electrically conductive in a direction through the medium and electrically insulating
(Continued)

in directions along the medium. An electrical circuit may be mechanically mounted to the circuit mounting portion of the first substrate via the anisotropic medium with at least one electrically conductive terminal juxtaposed over the at least one electrically conductive pad. The anisotropic medium may establish local electrical contact between the at least one electrically conductive terminal and the at least one electrically conductive pad.

23 Claims, 9 Drawing Sheets

(51) Int. Cl.
*A61B 5/00* (2006.01)
*H05K 1/14* (2006.01)
*H05K 3/32* (2006.01)

(56) References Cited

U.S. PATENT DOCUMENTS

| | | |
|---|---|---|
| 6,554,798 B1 | 4/2003 | Mann et al. |
| 6,560,471 B1* | 5/2003 | Heller .................. A61B 5/0002 600/309 |
| 6,565,509 B1 | 5/2003 | Say et al. |
| 6,565,532 B1 | 5/2003 | Yuzhakov et al. |
| 6,661,161 B1* | 12/2003 | Lanzo .................. B06B 1/0688 310/334 |
| 2002/0109124 A1 | 8/2002 | Ishimatsu |
| 2003/0114836 A1 | 6/2003 | Estes et al. |
| 2004/0167464 A1 | 8/2004 | Ireland et al. |
| 2005/0096513 A1* | 5/2005 | Ozguz ................ H01L 21/6836 600/301 |
| 2005/0106713 A1* | 5/2005 | Phan ...................... A61B 5/157 435/287.2 |
| 2006/0016700 A1* | 1/2006 | Brister ................ A61B 5/1411 205/777.5 |
| 2007/0060869 A1 | 3/2007 | Tolle et al. |
| 2007/0060870 A1 | 3/2007 | Tolle et al. |
| 2009/0261483 A1 | 10/2009 | Katogi et al. |

OTHER PUBLICATIONS

"Anisotropic Conductive Firm Adhesive" Product Selection Guide, Jan. 2007, 3M Electronics, USA XP002488597 (7 pages).

* cited by examiner

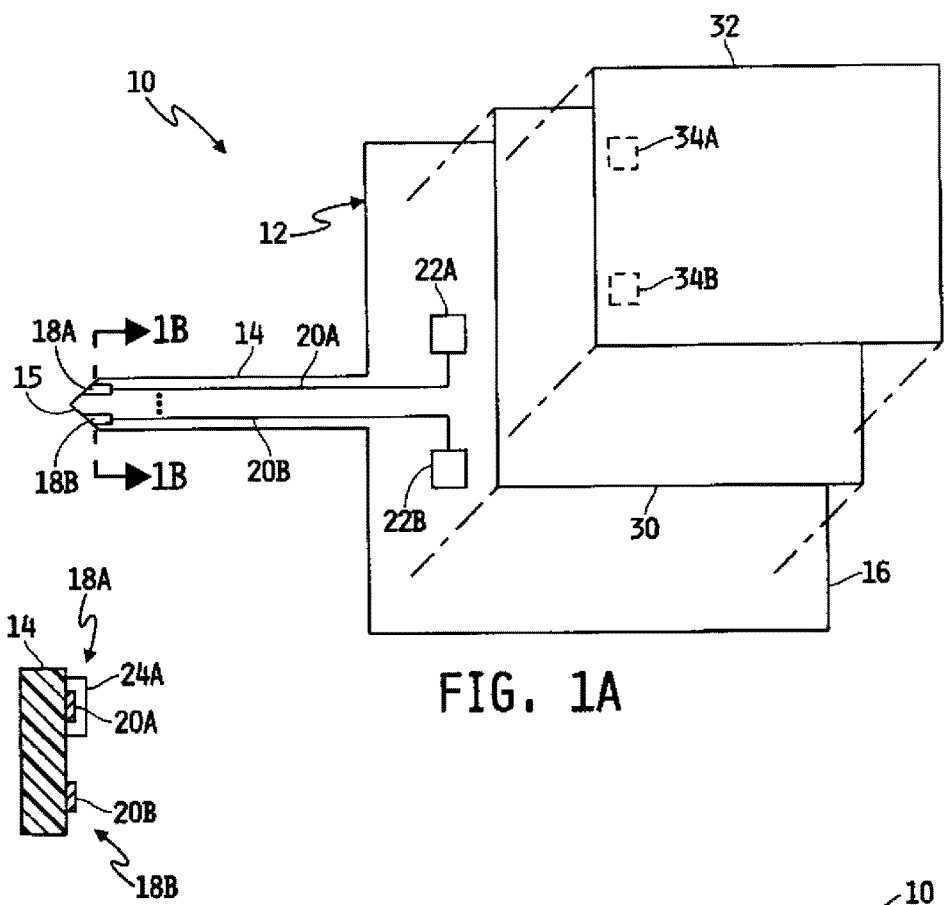
FIG. 1A
FIG. 1B
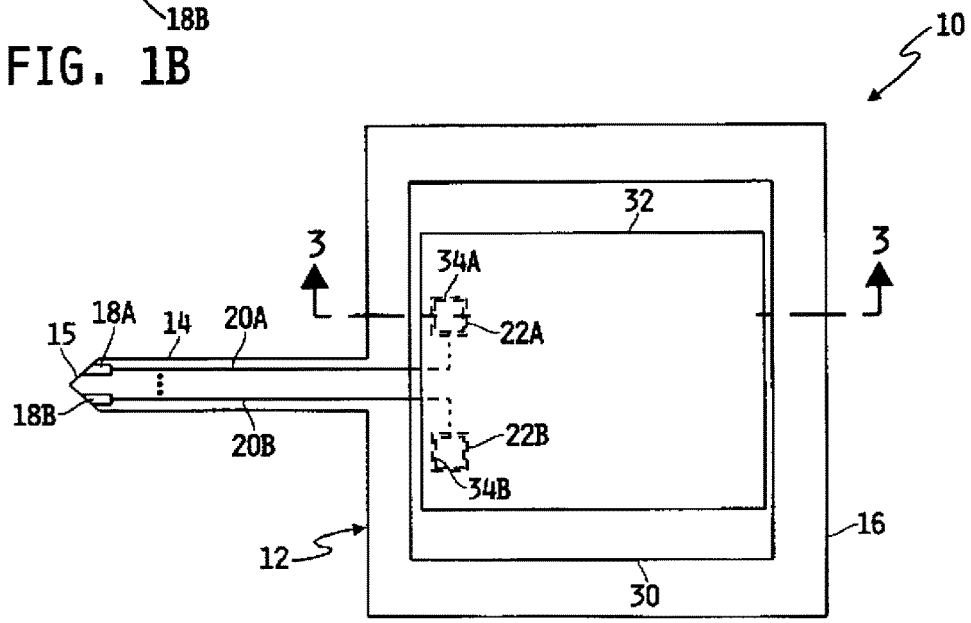
FIG. 2

SENSOR FOR MONITORING A CONDITION OF A PATIENT

This application claims the benefit, under 35 U.S.C. §119(e), of U.S. patent application Ser. No. 11/742,998 filed May 1, 2007, which is hereby expressly incorporated by reference.

FIELD OF THE INVENTION

The present invention relates generally to sensors for determining a condition of a patient, and more specifically to techniques for mating sensors of this type with electrical circuitry.

BACKGROUND

It is generally known to use one or more sensors to monitor a condition of a patient. It is desirable to mount electrical circuitry to such sensors to control sensor operation and/or perform other functions.

SUMMARY

The present invention may comprise one or more of the features recited in the attached claims, and/or one or more of the following features and combinations thereof. One embodiment of a sensor may comprise a first substrate, an anisotropic medium and an electrical circuit. The first substrate may have a sensing portion configured to be percutaneously inserted into a patient and an extracorporeal circuit mounting portion. The sensing portion may define a sensor thereon. The sensor may be configured to produce a signal indicative of a condition of the patient. The circuit mounting portion may have at least one electrically conductive pad formed thereon that is electrically connected to the sensor. The anisotropic medium may be disposed on the circuit mounting portion of the first substrate. The medium may be configured to be electrically conductive in a direction through the medium and electrically insulating in directions along the medium. The electrical circuit may have at least one electrically conductive terminal. The circuit may be mechanically mounted to the circuit mounting portion of the first substrate via the anisotropic medium with the at least one electrically conductive terminal juxtaposed over the at least one electrically conductive pad. The anisotropic medium may establish local electrical contact between the at least one electrically conductive terminal and the at least one electrically conductive pad. The first substrate may be a flexible substrate or a rigid substrate.

The anisotropic medium may be an anisotropic tape configured to mechanically bond the electrical circuit to the circuit mounting portion of the first substrate. The anisotropic tape may be electrically insulating along a plane of the tape and electrically conductive through the tape in a direction generally perpendicular to the plane of the tape. The anisotropic medium may alternatively or additionally be an anisotropic elastomer configured to mechanically bond the circuit to the circuit mounting portion of the first substrate. The anisotropic elastomer may be electrically insulating along a plane generally parallel to opposing surfaces of the electrical circuit and the circuit mounting portion of the first substrate, and electrically conductive through the elastomer in a direction generally perpendicular to the plane.

The first substrate may define a first number of electrically conductive pads on the circuit mounting portion thereof, and the electrical circuit may have a second number of electrical terminals. At least some of the second number of electrical terminals may align with at least some of the number of electrically conductive pads when the electrical circuit is mounted to the circuit mounting portion of the first substrate.

The electrical circuit may comprise a second substrate defining the at least one electrical terminal. The second substrate may be a flexible substrate or a rigid substrate. A number of electrical components may be mounted to the second substrate and electrically interconnected to form a sensor control circuit. The sensor control circuit may be electrically connected to the at least one electrical terminal. The sensor control circuit may include a sensor operating circuit configured to operate the sensor. The sensor control circuit may additionally include a telemetry circuit configured to transmit or receive communication signals to or from a first remote electronic device. The sensor control circuit may alternatively or additionally include a notification circuit configured to produce any of a visual, audible and tactile indication of a predefined event. The sensor control circuit may be configured to determine the predefined event from the signal produced by the sensor. In such embodiments, the first remote electronic device may include a first telemetry circuit configured to transmit or receive wireless communication signals to or from the telemetry system of the sensor control circuit. The telemetry circuit of the sensor control circuit may be configured to transmit a wireless signal indicative of the predefined event to the first telemetry circuit of the first remote electronic device. The sensor control circuit may alternatively or additionally include an acknowledgement circuit responsive to user activation thereof to acknowledge production of the visual, audible or tactile indication of the predefined event. A second remote electronic device may be further included, as well as a means for establishing communications between the first and second remote electronic devices. For example, the first remote electronic device may include a second telemetry circuit configured to transmit or receive wireless communication signals to or from a second remote electronic device.

The electrical circuit may define an outer periphery that is contained within an outer periphery of the circuit mounting portion of the first substrate when the electrical circuit is mounted thereto.

Another embodiment of a sensor may comprise first, second and third substrates. The first substrate may have a sensing portion configured to be percutaneously inserted into a patient and an extracorporeal circuit mounting portion. The sensing portion may define a sensor thereon. The sensor may be configured to produce a signal indicative of a condition of the patient. The circuit mounting portion may have at least one electrically conductive pad defined thereon that is electrically connected to the sensor. The second substrate may be mounted to the first substrate and may define therethrough at least one passageway that is aligned with the at least one electrically conductive pad defined on the first substrate. The third substrate may be mounted to the second substrate and may define thereon at least one electrical terminal. The at least one electrical terminal may align with at least one passageway defined on the second substrate and with the at least one electrically conductive pad defined on the first substrate. A first number of electrical components may be mounted to the third substrate and may be electrically interconnected to form a sensor control circuit. The sensor control circuit may be electrically connected to the at least one electrical terminal defined on the third substrate. Means may be provided for establishing electrical contact through the at least one passageway between the at least one electrically conductive pad defined on the first substrate and the at least one electrical terminal defined on the third substrate, to thereby electrically connect the sensor to the sensor control circuit.

The sensor control circuit may include a telemetry circuit configured to transmit or receive communication signals to or from a first remote electronic device. Alternatively or additionally, the sensor control circuit may include a notification circuit configured to produce any of a visual, audible and tactile indication of a predefined event. In such embodiments, the sensor control circuit may be configured to determine the predefined event from the signal produced by the sensor. Alternatively or additionally, the sensor control circuit may include an acknowledgement circuit responsive to user activation thereof to acknowledge production of the visual, audible or tactile indication of the predefined event.

In embodiments wherein the sensor control circuit includes a telemetry circuit, the first remote electronic device may include a first telemetry circuit configured to transmit or receive communication signals to or from the telemetry system of the sensor control circuit. The telemetry circuit of the sensor control circuit may be configured to transmit a signal indicative of the predefined event to the first telemetry circuit of the first remote electronic device. A second remote electronic device may be further included, as well as a means for establishing communications between the first and second remote electronic devices. For example, the first remote electronic device may include a second telemetry circuit configured to transmit or receive wireless communication signals to or from a second remote electronic device.

The first substrate may define a first number of electrically conductive pads on the circuit mounting portion thereof. The third substrate may define a second number of electrical terminals thereon. The second substrate may define a corresponding second number of passageways therethrough. At least some of the second number of electrical terminals may align with at least some of the first number of electrically conductive pads through corresponding ones of the second number of passageways defined through the second substrate when the second substrate is mounted to the first substrate and the third substrate is mounted to the second substrate.

The first substrate may be a flexible substrate or a rigid substrate. The second substrate may be a flexible substrate or a rigid substrate. The third substrate may be a flexible substrate or a rigid substrate.

A second number of electrical components may be mounted to the second substrate. The second number of electrical components and the first number of electrical components may together form the sensor control circuit. Means may be provided for electrically connecting the second number of electrical components to the first number of electrical components. The second number of electrical components may include a sensor operating circuit configured to operate the sensor. Alternatively or additionally, the second number of electrical components may include a telemetry circuit configured to transmit or receive communication signals to or from a remote electronic device. Alternatively or additionally, the second number of electrical components may include a notification circuit configured to produce any of a visual, audible and tactile indication of a predefined event. Alternatively or additionally, the second number of electrical components may include an acknowledgement circuit responsive to user activation thereof to acknowledge production of the visual, audible or tactile indication of the predefined event. In one example embodiment, the second number of electrical components may include a sensor operating circuit configured to operate the sensor, and the first number of electrical components may include a telemetry circuit configured to transmit or receive communication signals to or from a remote electronic device. In this embodiment, the second number of electrical components may include a notification circuit configured to produce any of a visual, audible and tactile indication of a predefined event. In this embodiment, the second number of electrical components may alternatively or additionally include an acknowledgement circuit responsive to user activation thereof to acknowledge production of the visual, audible or tactile indication of the predefined event.

Yet another embodiment of a sensor may comprise first, second and third substrates. The first substrate may have a sensing portion configured to be percutaneously inserted into a patient and an extracorporeal circuit mounting portion. The sensing portion may define a sensor thereon. The sensor may be configured to produce a signal indicative of a condition of the patient. The circuit mounting portion may have at least one electrically conductive pad defined thereon that is electrically connected to the sensor. The second substrate may be mounted to the first substrate and may define thereon a first number of electrically conductive pads. At least one of the first number of electrically conductive pads may be aligned with the at least one electrically conductive pad defined on the first substrate and at least another of the first number of electrically conductive pads defined on the second substrate may be electrically connected to the at least one of the first number of electrically conductive pads defined on the second substrate. Means may be provided for establishing electrical contact between the at least one electrically conductive pad defined on the first substrate and the at least one of the first number of electrically conductive pads defined on the second substrate. The third substrate may be mounted to the second substrate and may define thereon the at least one electrical terminal. A first number of electrical components may be mounted to the third substrate and may be electrically interconnected to form a sensor control circuit. The sensor control circuit may be electrically connected to the at least one electrical terminal defined on the third substrate. Means may be provided for establishing electrical contact between the at least another of the first number of electrically conductive pads defined on the second substrate and the at least one electrical terminal defined on the third substrate to thereby electrically connect the sensor to the sensor control circuit.

The sensor control circuit may include a telemetry circuit configured to transmit or receive communication signals to or from a first remote electronic device. Alternatively or additionally, the sensor control circuit may include a notification circuit configured to produce any of a visual, audible and tactile indication of a predefined event. In such embodiments, the sensor control circuit may be configured to determine the predefined event from the signal produced by the sensor. Alternatively or additionally, the sensor control circuit may include an acknowledgement circuit responsive to user activation thereof to acknowledge production of the visual, audible or tactile indication of the predefined event.

In embodiments wherein the sensor control circuit includes a telemetry circuit, the first remote electronic device may include a first telemetry circuit configured to transmit or receive communication signals to or from the telemetry system of the sensor control circuit. The telemetry circuit of the sensor control circuit may be configured to transmit a signal indicative of the predefined event to the first telemetry circuit of the remote electronic device. A second remote electronic device may be further included, as well as a means for establishing communications between the first and second remote electronic devices. For example, the first remote electronic device may include a second telemetry circuit configured to transmit or receive wireless communication signals to or from a second remote electronic device.

The first substrate may be a flexible substrate or a rigid substrate. The second substrate may be a flexible substrate or a rigid substrate. The third substrate may be a flexible substrate or a rigid substrate.

The first substrate may define a second number of electrically conductive pads on the circuit mounting portion thereof. At least some of the first number of electrically conductive pads defined on the second substrate may align with corresponding ones of the second number of electrically conductive pads defined on the circuit mounting portion of the first substrate when the second substrate is mounted to the first substrate. The third substrate may define a third number of electrical terminals thereon. At least others of the first number of electrically conductive pads defined on the second substrate may align with corresponding ones of the third number of electrical terminals defined on the third substrate. Alternatively or additionally, means may be provided for electrically connecting at least others of the first number of electrically conductive pads defined on the second substrate to corresponding ones of the third number of electrical terminals defined on the third substrate.

A second number of electrical components may be mounted to the second substrate. The second number of electrical components and the first number of electrical components may together form the sensor control circuit. Means may be provided for electrically connecting the second number of electrical components to the first number of electrical components. The second number of electrical components may include a sensor operating circuit configured to operate the sensor. Alternatively or additionally, the second number of electrical components may include a telemetry circuit configured to transmit or receive communication signals to or from a remote electronic device. Alternatively or additionally, the second number of electrical components may include a notification circuit configured to produce any of a visual, audible and tactile indication of a predefined event. Alternatively or additionally, the second number of electrical components may include an acknowledgement circuit responsive to user activation thereof to acknowledge production of the visual, audible or tactile indication of the predefined event. In one example embodiment, the second number of electrical components may include a sensor operating circuit configured to operate the sensor, and the first number of electrical components may include a telemetry circuit configured to transmit or receive communication signals to or from a remote electronic device. In this embodiment, the second number of electrical components may include a notification circuit configured to produce any of a visual, audible and tactile indication of a predefined event. In this embodiment, the second number of electrical components may alternatively or additionally include an acknowledgement circuit responsive to user activation thereof to acknowledge production of the visual, audible or tactile indication of the predefined event.

BRIEF DESCRIPTION OF THE DRAWINGS

FIG. 1A is an assembly view of one embodiment of a sensor module including a sensor and an electrical circuit mountable thereto.

FIG. 1B is a cross-sectional view of the sensing portion of the module of FIG. 1A taken along section lines 1B-1B.

FIG. 2 is an assembled view of the sensor module of FIGS. 1A and 1B.

DESCRIPTION OF THE ILLUSTRATIVE EMBODIMENTS

Figure 4:
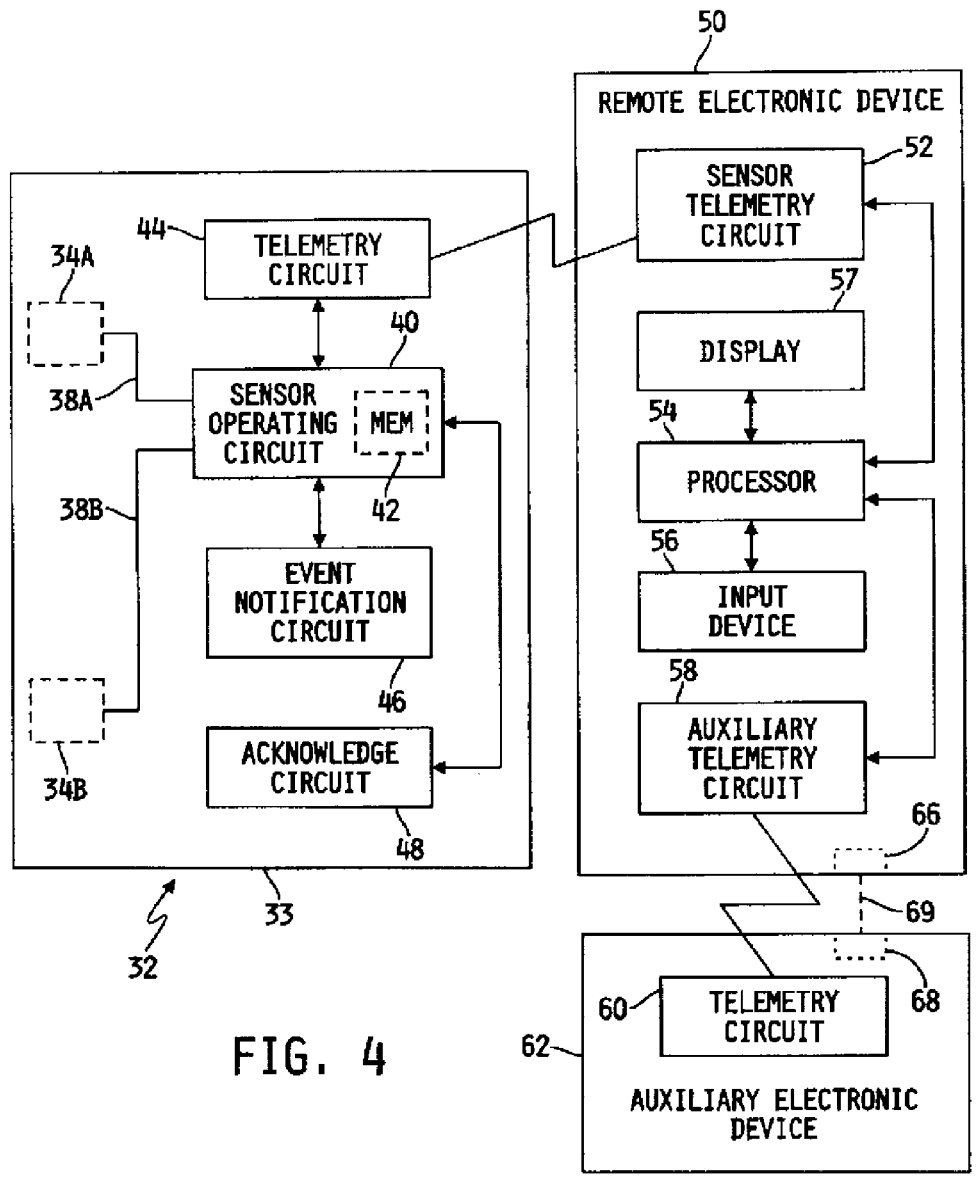
FIG. 4 is a block diagram illustrating one embodiment of the electrical circuit illustrated generally in FIGS. 1A, 2 and 3.

For the purposes of promoting an understanding of the principles of the invention, reference will now be made to a number of illustrative embodiments shown in the attached drawings and specific language will be used to describe the same.

Referring now to FIGS. 1A, 1B and 2, one illustrative embodiment of a sensor module 10 is shown that includes a sensor-carrying substrate 12 having an electrical circuit 32 mountable thereto. In the illustrated embodiment, the substrate 12 includes a sensing portion 14 that is configured for percutaneous insertion into a patient (e.g., into tissue, vein or artery) and an extracorporeal circuit mounting portion 16.

The sensing portion 14 of the substrate 12 includes a sensor in the form of at least one working electrode 18A and at least one auxiliary electrode 18B formed thereon adjacent to an insertion tip 15 of the sensing portion 14. The auxiliary electrode 18B may be, depending upon the application, part of the working electrode 18A, another working electrode separate from the working electrode 18A, a counter electrode or a reference electrode. It will be understood that the sensor 18A,B may alternatively include additional or fewer electrodes formed on any side of the sensing portion 14 of the substrate 12, and that any such sensor electrodes may be located anywhere along the sensing portion 14. Alternatively still, the auxiliary electrode 18B and/or one or more additional electrodes associated with the sensor 18A,B may be formed on a different structure that is implanted within, inserted into or otherwise in contact with the patient.

The sensor electrodes 18A and 18B are formed using electrically conductive traces 20A and 20B respectively that are disposed on the substrate 12 in a conventional manner. A sensing layer may be formed on, over or near either electrode 18A or 18B, or on, over or near both electrodes 18A and 18B, and in the illustrated embodiment a sensing layer 24A is formed over the electrode 18A. The sensing end 15 of the sensing portion 14 may be configured, as illustrated in FIGS. 1A and 2, to facilitate percutaneous insertion of the sensing portion 14 into a patient.

In the illustrated embodiment, the working electrode 18A is covered near the insertion end 15 of the sensing portion 14 of the substrate 12 with a sensing layer 24A. The sensing layer 24A may be formed using conventional materials that facilitate the electrochemical detection of an analyte or other condition of the patient's body when the analyte or other condition cannot be otherwise electrolyzed at a specified rate and/or with a specified accuracy using only the underlying working electrode 18A. Illustratively, the sensing layer 24A may include a conventional electron transfer agent that transfers electrons directly or indirectly between an analyte and the working electrode 18A. The sensing layer 24A may also contain a conventional catalyst to catalyze a reaction of the analyte. In other embodiments, the working electrode 18A may have a sensing layer 24A that does not contain either an electron transfer agent.

In the illustrated embodiment, the sensing layer 24A is disposed directly on the electrically conductive portion 20A of the working electrode 18A. In other embodiments, the sensing layer 24A may be spaced apart from the electrically conductive portion 20A of the working electrode 18A by one or more conventional separation layers (not shown). Such separation layers typically include one or more membranes or films, and in addition to separating the electrically conductive portion 20A of the working electrode 18A from the sensing layer 24A, the one or more separation layers may also act as a conventional mass transport limiting layer or a conventional interferent eliminating layer. In other embodiments, the sensing layer 24A may comprise two or more conventional sensing layers (not shown). The sensing layer or layers 24A may additionally include other operationally enhancing materials and/or layers including, but not limited to, a biocompatible layer, and/or other optional layers and/or components. In still other embodiments, the working electrode 18A may not include a sensing layer 24A.

The auxiliary electrode 18B may be formed using a suitably conductive material, and example of which may be, but should not be limited to, silver/silver chloride. Alternatively, the electrode 18B may be coated with or bound to a suitable material, at or near the insertion end 15 of the sensing portion 14 that enhances operation of the electrode 18B another working electrode, counter electrode or reference electrode. It is desirable for the surface of the electrode 18B to be non-corroding to facilitate accurate sensor operation.

The substrate 12 may be formed using any one or combination of conventional, electrically non-conducting materials that are by themselves, or that may be further processed to be, suitable for in-vivo use. In one embodiment, the substrate 12 is flexible, and in one specific embodiment the substrate 12 is made of Melinex® polyester film (e.g., polyethylene terephthalate). Other suitable materials for a flexible substrate 12 include, for example, but are not limited to, electrically insulating plastic or polymeric materials such as polycarbonates, other polyesters such as Mylar®, polyvinyl chloride, polyurethanes, polyethers, polyimides, or copolymers of thermoplastics, such as glycol-modified polyethylene terephthalate, and/or other electrically non-conducting, flexible, deformable materials. In other embodiments, the substrate 12 is rigid, and may be made using conventional electrically non-conducting materials. Examples of such rigid, electrically non-conducting materials include, but are not limited to, ceramics, such as aluminum oxide and silicon dioxide, and the like. Combinations of flexible and non-flexible materials are also contemplated.

The substrate 12 is sized so that at least a portion of the tip 15 of the sensing portion 14 can be percutaneously inserted into a patient, such that the one or more sensor electrodes, e.g., 18A and/or 18B, are suitably positioned to monitor a condition, e.g., an analyte such as blood glucose, temperature, blood pressure, or the like, of the patient, and while the circuit mounting portion 16 remains extracorporeal. The circuit mounting portion 16 is sized to accommodate the mounting of an electrical circuit 32 thereto as will be described in greater detail hereinafter. The circuit mounting portion 16 is also sized to accommodate placement thereon of a number of electrically conductive pads that are each electrically connected to a corresponding one of the sensor electrodes. In the illustrated embodiment, for example, wherein two such sensor electrodes 18A and 18B are shown, two corresponding electrically conductive pads 22A and 22B are formed on the circuit mounting portion 16 of the substrate 12. The electrically conductive pad 22A is electrically connected to the sensor electrode 18A via an electrically conductive trace 20A formed on the sensing and circuit mounting portions 14 and 16 respectively, and the electrically conductive pad 20B is electrically connected to the sensor electrode 18B via another electrically conductive trace 20B formed on the sensing and circuit mounting portions 14 and 16 respectively. It will be understood, however, that the substrate 12 may include more or fewer sensor electrode, electrically conductive pad and interconnecting trace combinations.

The electrically conductive traces, e.g., 20A and 20B, and the electrically conductive pads, e.g., 22A and 22B, may be formed on the substrate 12 by any of a variety of conventional techniques. Examples of conventional techniques for forming such electrically conductive traces and electrically conductive pads include, but are not limited to, laser ablation, photolithography, screen printing, wet or dry etching of deposited conductive material, or other conventional techniques. Examples of electrically conductive materials used to form the electrically conductive traces and pads include, but are not limited to, carbon, e.g., graphite, conductive polymers, metals or alloys, metallic compounds, or the like. The formation of films of carbon, conductive polymer, metal, alloy, or metallic compound are well-known and include, for example, but are not limited to, chemical vapor deposition (CVD), physical vapor deposition, sputtering, reactive sputtering, printing, coating, and painting. It will be understood that the electrically conductive pads, e.g., 22A and 22B, may, but need not, be formed of the same material used to form the electrically conductive traces, e.g., 20A and 20B.

Figure 3:
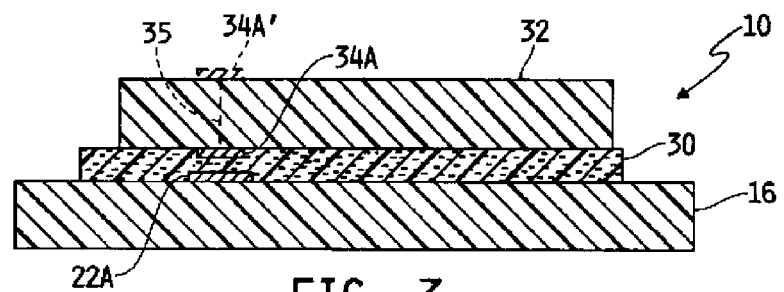
FIG. 3 is a cross-sectional view of the sensor module of FIG. 2 taken along section lines 3-3.
Figure 5:
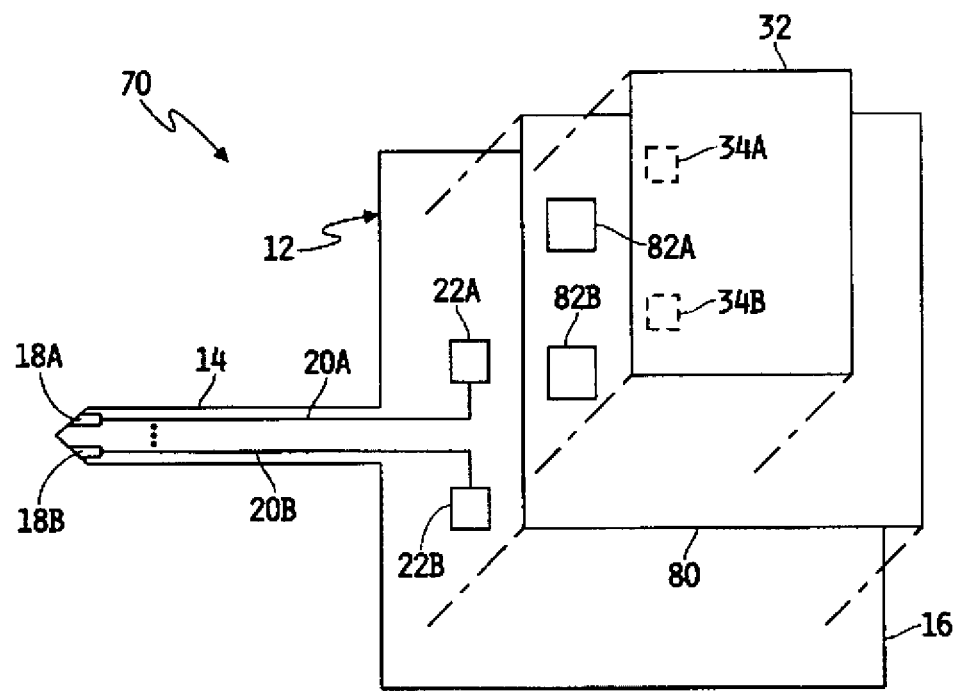
FIG. 5 is an assembly view of another embodiment of a sensor module including a sensor and an electrical circuit mountable thereto.

The electrical circuit 32 defines one or more electrical terminals that align with one or more corresponding electrically conductive pads formed on the circuit mounting portion 16 of the substrate 12 when the electrical circuit 32 is juxtaposed over the circuit mounting portion 16. The one or more electrical terminals are electrically connected to sensor control circuitry carried by, formed on, or otherwise defined by the electrical circuit 32. The one or more electrical terminals may be variously shaped and/or sized, and in one embodiment are provided in the form of one or more electrically conductive pads. In the illustrated embodiment, for example, the electrical circuit 32 defines two such electrically conductive pads 34A and 34B which align with the electrically conductive pads 22A and 22B respectively on the circuit mounting portion 16 of the substrate 12 when the electrical circuit 32 is juxtaposed over the circuit mounting portion 16 as shown in FIGS. 2 and 3. It will be understood that the number of electrically conductive pads formed on the circuit mounting portion 16 of the substrate 12 may be equal to, less than or greater than the number of electrical terminals defined by the electrical circuit 32. In any of these cases, however, at least one of the electrical terminals defined by the electrical circuit 32 aligns with at least one of the electrically conductive pads formed on the circuit mounting portion 16 of the substrate 12 when the electrical circuit 32 is juxtaposed over the circuit mounting portion 16 so that electrical connected may be established therebetween. At least some of the number of electrically conductive pads defined on the circuit mounting portion 16 of the substrate 12 may be arranged to form a pattern, e.g., a bit pattern, that contains identification information and/or other information relating to the sensor 18A,B, substrate 12 or combination thereof. Such a bit pattern is then detectable by the electrical circuit 32 when electrical connection is established between the electrically conductive pads that define the bit pattern and corresponding ones of the electrical terminals defined by the electrical circuit 32. In this embodiment, the electrical circuit 32 may thus determine information relating to the sensor 18A,B, the substrate 12 and or the combination thereof based only on the pattern of electrical connections therebetween. The electrical circuitry 32 may be configured to activate on-board notification circuitry and/or to wirelessly transmit signals to a remote electronic device, that are indicative of the information contained in the bit pattern and/or that are the result of further processing of this information.

An anisotropic medium 30 is disposed between the electrical circuit 32 and the circuit mounting portion 16 of the substrate 12. The anisotropic medium 30 has adhesive properties which serve to mechanically attach or mount the electrical circuit 32 to the circuit mounting portion 16 of the substrate 12. The anisotropic medium 32 is also electrically conductive in a direction through the medium but is electrically insulating in a direction along or across the medium. By suitably positioning the one or more electrically conductive pads, e.g., pads 22A and 22B on the circuit mounting portion 16 of the substrate 12 and/or by suitably positioning the one or more electrical terminals on the electrical circuit 32 so that one or more of the electrical terminals align with one or more of the electrically conductive pads when the circuit 32 is juxtaposed over the circuit mounting portion 16 of the substrate 12, local electrical contact is established therebetween when the components 16, 30 and 32 are assembled as illustrated in FIGS. 2 and 3.

In one embodiment, the anisotropic medium 30 may be provided in the form of a conventional anisotropic electrically conductive adhesive tape. The tape in this embodiment is a flexible adhesive matrix filled with electrically conductive particles that provide electrical connectivity in a direction through the plane of the tape, but which are spaced sufficiently far apart so that the tape is electrically insulating in directions along the plane of the tape. The anisotropic adhesive tape 30 is disposed between the circuit mounting portion 16 of the substrate 12 and the electrical circuit 32, as shown in FIGS. 2 and 3. When the electrical circuit 32 is pressed into the tape 30 with the electrical terminals 34A and 34B aligned with the electrically conductive pads 22A and 22B, local electrical contact is established through the tape 30, in a direction that is generally perpendicular to the plane of the tape 30, between the electrical terminals 34A, 34B and corresponding electrically conductive pads 22A, 22B. Alternatively, the anisotropic medium 30 may be provided in the form of an anisotropic electrically conductive elastomer, such as an adhesive film, having the same properties just described with respect to the anisotropic electrically conductive adhesive tape. In this embodiment, the elastomer 30 defines a plane generally parallel to opposing surfaces of the electrical circuit 32 and the circuit mounting portion 16 of the substrate 12, and the elastomer 30 is electrically insulating in directions along or parallel to the plane and electrically conductive in a direction generally perpendicular to the plane.

One example of the anisotropic electrically conductive medium 30 may be or include one or more anisotropic conductive film adhesives that are commercially available from 3M™ Electronics of St. Paul, Minn. Examples include, but are not limited to, 3M™ products 7303, 7313, 8794, 5460R, 5552R, 7373 and 9703. Some such products, e.g., 9703, are available in the form of anisotropic, electrically-conductive adhesive transfer tape, which is a pressure sensitive tape that does not require thermal bonding. Generally, 9703 is a flexible tape that is randomly loaded with electrically conductive particles. When force is applied to the tape along its Z-axis, the conductive particles contact one another in the area of the force. In the bonding of electrical circuitry, the result is that the tape becomes electrically conductive along the Z-axis at the bonding areas, but is electrically insulating along the plane of the tape. The remaining products described above are available in the form of anisotropic (electrically) conductive film (ACF) adhesives, where are heat-bondable, Z-axis conductive films containing thermoplastic and thermoset adhesives randomly loaded with electrically conductive particles. Electrical contact is made in the same manner described with respect to the anisotropic, electrically-conductive adhesive transfer tape, and the product is cured to form a permanent bond by applying heat during the bonding process.

In one experimental setup, one of the 3M™ ACF adhesives was used to bond FR4 circuit boards 32 of thickness 1.6 mm to Melinex® substrates 12 forming part of a sensor as shown in FIGS. 1 and 2. In this experiment, circuit boards 32 were successfully bonded to substrates 12, with electrical contact established between the contacts 22A/34A and 22B/34B, by forcing a flat surface of a brass block, heated to 135° C., perpendicularly onto the Melinex® film 12 using a linear guide supported on ball bearings. A spring, k=2 kg/mm, was used to apply a force of 11.7 kg to the brass block. The spring travel was set to 5.6 mm, and the brass block was forced against the substrate 12 for approximately 50 seconds, after which the substrate 12 was slightly displaced, and the brass block was again forced against the substrate 12 for another 20-30 seconds. It will be understood that the results of this experiment are provided only for illustrative purposes, and should not be considered to be limiting in any way.

In any case, a substantial portion of the circuit mounting portion 16 of the substrate 12 and the electrical circuit 32 are covered by the anisotropic medium 30, thereby resulting in a strong mechanical attachment of the electrical circuit 32 to the substrate 12. In the illustrated embodiment, for example, the electrical circuit 32 defines an outer periphery that is contained within an outer periphery of the circuit mounting portion 16 of the substrate 12 when the electrical circuit 32 is mounted thereto. In this embodiment, one entire surface of the electrical circuit 32 is thus covered by the anisotropic medium. The present disclosure contemplates other embodiments wherein the outer periphery of the electrical circuit 32 extends to or beyond at least a portion of the outer periphery of the circuit mounting portion 16 of the substrate 12.

Referring now to FIG. 4, a block diagram of one illustrative embodiment of the electrical circuit 32 is shown. In the illustrated embodiment, the electrical circuit 32 is a sensor control circuit that includes a sensor operating circuit 40 having a conventional memory unit 42. The sensor operating circuit 40 includes a number of inputs that are each electrically connected to a corresponding one of the number of electrically conductive terminals defined by the electrical circuit 32. In the illustrated embodiment, for example, the sensor operating circuit includes two such inputs. A first input is electrically connected to the electrically conductive terminal 34A via a signal path 38A, and a second input is electrically connected to the electrically conductive terminal 34B via another signal path 38B.

The sensor operating circuit 40 includes conventional circuitry for operating the sensor 18A, 18B such as by, for example, providing appropriate voltages across the sensor electrodes 18A and 18B and collecting signals produced by the sensor 18A, 18B. The sensor control circuit 40 may also be configured to process the signals produced by the sensor 18A, 18B, and to then control one or more electrical circuits on-board the electrical circuit 32 and/or external to the electrical circuit 32. In one embodiment, the sensor control circuit 40 is microprocessor-based, and is operable to execute one or more software algorithms stored in the memory unit 42 to control operation of the sensor 18A, 18B and/or additional circuitry on-board and/or external to the electrical circuit 32.

The sensor control circuit 32 may illustratively include a conventional telemetry circuit 44 that is electrically connected to the sensor operating circuit 42. The telemetry circuit 44 may be configured to wirelessly transmit signals to a remote electronic device 50, and/or to receive signals from the remote electronic device 50. The telemetry circuit 44 may be controlled by the sensor operating circuit 40 to transmit and/or receive specified information, or may alternatively be controlled by the sensor operating circuit 40 only to transmit information and to be responsive to signals transmitted by the remote electronic device 50 to receive information. In any case, the telemetry circuit 44 may be configured to conduct wireless communication using any conventional wireless communication techniques. Examples of such conventional wireless communications techniques include, but are not limited to, infrared (IR) communications, radio frequency (RF) communications, inductively coupled communications, or the like.

The sensor control circuit 32 may also illustratively include a conventional event notification circuit 46 that is electrically connected to the sensor operating circuit 42. The event notification circuit 46 is configured to provide a notification of a specified event, and may accordingly include any one or more conventional visual, audible and/or tactile indication devices. The event notification circuit 46 is configured to be responsive to an event notification signal to activate the one or more visual, audible and/or tactile indication devices according to any desired indication pattern. The event that triggers activation of the one or more visual, audible and/or tactile indication devices of the event notification circuit 46 generally results from information provided by the sensor 18A, 18B. In the illustrated embodiment, the sensor operating circuit 40 is operable to process all information produced by the sensor 18A, 18B, and is accordingly operable to determine the event that triggers activation of the event notification circuit 46 from the signals produced by the sensor 18A, 18B. Upon determining such an event, the sensor operating circuit 40 is then operable to control activation of the event notification circuit 46. Alternatively, the sensor operating circuit 40 may be operable, upon determining such an event, to control the telemetry circuit 44 transmit a wireless event signal, which may be received by a sensor telemetry circuit 52 that forms part of the remote electronic device 50.

The sensor control circuit 32 may also illustratively include an acknowledge circuit 48 that is electrically connected to the sensor operating circuit 40. The acknowledge circuit 48 is configured to be responsive to user activation thereof to produce an acknowledgement signal, and to provide the acknowledgement signal to the sensor operating circuit 40. Generally, the acknowledge circuit 48 is provided as a mechanism for the user to acknowledge production of the visual, audible or tactile indication of the predefined event. In this regard, the acknowledge circuit 48 may include any conventional user activation mechanism including, for example, but not limited to, a user activated button, switch or the like.

The sensor control circuit 32 may be implemented in any of a variety of conventional forms. In one embodiment, for example, the sensor control circuit 32 may be a single, monolithic integrated circuit configured to include at least the sensor operating circuit 40, and to optionally include any one or more of the telemetry circuit 44, the event notification circuit 46 and the acknowledgement circuit 48. In this embodiment, the one or more electrical terminals comprise one or more electrically conductive circuit terminals or leads extending from a hermetically sealed integrated circuit package containing the integrated circuit. In this embodiment, the structure 33 thus represents a packaged integrated circuit. In another embodiment, for example, the sensor control circuit 32 may include a sensor control circuit substrate having at least the sensor operating circuit 40, and optionally any one or more of the telemetry circuit 44, the event notification circuit 46 and the acknowledgement circuit 48, mounted thereto. In this embodiment, the structure 33 illustrated in FIG. 4 represents the sensor control circuit substrate. The substrate 33 may be flexible or rigid, and the one or more electrical terminals may take the form of one or more electrically conductive pads formed on the underside of the substrate 33, one or more circuit traces formed on the underside of the substrate 33 or one or more electrical conductors extending from the underside of the substrate 33. In this embodiment, the sensor operating circuit 40, and optionally any one or more of the telemetry circuit 44, the event notification circuit 46 and the acknowledgement circuit 48, is mounted to a top side of the substrate 33, and the one or more electrical terminals defined on the underside of the substrate 33 are electrically connected to corresponding electrical terminals or circuit traces defined on the top side of the substrate 33 in a conventional manner. An example of this is illustrated in FIG. 3 where the electrical terminal 34A defined on the bottom surface of the sensor control circuit 32 is electrically connected via an electrical conductor 35 to an electrical terminal 34A' defined on the top surface of the sensor control circuit 32. The two electrical terminals 34A and 34A' may be electrically connected using conventional techniques including, for example, but not limited to, plated-though hole technology, using multiple layers of conductors interconnected by vias, wrapping electrically conductive circuit traces around the substrate from the top surface to the bottom surface, and the like. Examples of suitable flexible materials that may be used to implement the substrate 33 in flexible form include, but are not limited to, Melinex® polyester film (e.g., polyethylene terephthalate), other polyesters such as Mylar®, polyvinyl chloride, electrically insulating plastic or polymeric materials such as polycarbonates, polyurethanes, polyethers, polyimides, or copolymers of thermoplastics, such as glycol-modified polyethylene terephthalate, and/or other electrically non-conducting, flexible, deformable materials. Examples of suitable rigid materials that may be used to implement the substrate 33 in rigid form include, but are not limited to, ceramics, such as aluminum oxide and silicon dioxide, conventional printed circuit boards, conventional multi-layer printed circuit boards, and the like. Combinations of flexible and non-flexible materials are also contemplated.

As described hereinabove, a remote electronic device 50 may include a sensor telemetry circuit 52 configured to wirelessly transmit signals to and/or receive signals from the telemetry circuit 44 of the sensor control circuit 32. The remote electronic device 50 may further include a conventional processor circuit 54, which may be implemented in the form of a conventional microprocessor that is electrically connected to the sensor telemetry circuit 52 and to an input device 56. An input device 56 may be or include a keyboard, key pad, touch screen display device, voice-activated device or the like, and may be used in a conventional manner to supply the processor 54 with information that may include, for example, commands to execute a desired function or process. A conventional display 57 may be included as part of the electronic device 50, and may be controlled by the processor 54 in a conventional manner to display messages, alerts and/or warnings in the form of one or more of a visual, audible or tactile form. In embodiments wherein the sensor operating circuit 40 of the electrical circuit 36 is operable to control the telemetry circuit 44 to transmit a wireless event signal, as described hereinabove, the telemetry circuit 52 of the electronic device 50 is operable to receive the wireless event signal and provide this signal to the processor 54. The processor 54 is, in turn, responsive to the wireless event signal to activate the display 57 to display, in visual, audible and/or tactile form, an indicator of the event.

The electronic device 50 may further include an auxiliary telemetry circuit 58 that is configured to transmit and/or receive wireless signals to and/or from a telemetry circuit 60 of another remote or auxiliary electronic device 62. Alternatively, the remote device 50 may include an input/output port 66, the remote or auxiliary device 62 may also include an input/output port 68, and a suitable wired connection 69 may electrically connect the input/output ports 66 and 68. Communication between the remote electronic device 50 and the remote or auxiliary electronic device 62 may be carried out using any conventional techniques and according to any conventional communications protocols.

Referring now to FIGS. 5-8, one illustrative embodiment of another sensor module 70 is shown. The sensor module 70 includes some of the same structural components as the sensor module 10 of FIGS. 1-4, and like numbers are therefore used to identify like components. In the illustrated embodiment, an intermediate substrate 80 is introduced between the circuit mounting portion 16 of the substrate 12 and the electrical circuit 32. The intermediate substrate 80 may be flexible or rigid, and in either case the substrate 80 defines therethrough one or more passageways that align with one or more corresponding electrically conductive pads defined on the circuit mounting portion 16 of the substrate 12 when the substrate 80 is mounted to the circuit mounting portion 16 of the substrate 12. In the illustrated embodiment, for example, the intermediate substrate 80 defines therethrough two such passageways 82A and 82B that align with corresponding electrically conductive pads 22A and 22B defined on the circuit mounting portion 16 of the substrate 12, and that are juxtaposed over the corresponding electrically conductive pads 22A and 22B when the substrate 80 is mounted to the circuit mounting portion 16 of the substrate 12. The substrate 80 may be attached to the circuit mounting portion 16 of the substrate 12 via a conventional attachment medium, and in the embodiment illustrated in FIG. 7 the substrate 80 is shown being attached or mounted to the mounting portion 16 of the substrate 12 via a conventional adhesive 84. Examples of other suitable attachment mechanisms include, but are not limited to, conventional epoxies or other formable or settable mediums, conventional adhesives including adhesive tapes, or the like. Examples of suitable flexible materials that may be used to implement the substrate 80 in flexible form include, but are not limited to, Melinex® polyester film (e.g., polyethylene terephthalate), other polyesters such as Mylar®, polyvinyl chloride, electrically insulating plastic or polymeric materials such as polycarbonates, polyurethanes, polyethers, polyimides, or copolymers of thermoplastics, such as glycol-modified polyethylene terephthalate, and/or other electrically non-conducting, flexible, deformable materials. Examples of suitable rigid materials that may be used to implement the substrate 80 in rigid form include, but are not limited to, ceramics, such as aluminum oxide and silicon dioxide, conventional printed circuit boards, conventional multi-layer printed circuit boards, and the like. Combinations of flexible and non-flexible materials are also contemplated.

Figure 6:
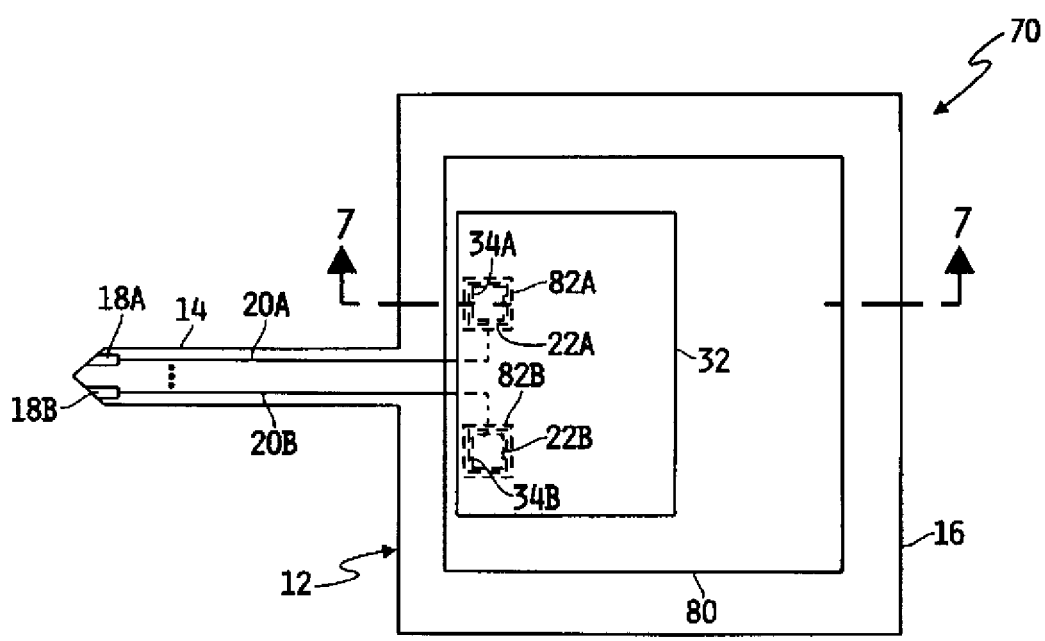
FIG. 6 is an assembled view of the sensor module of FIG. 5.
Figure 7:
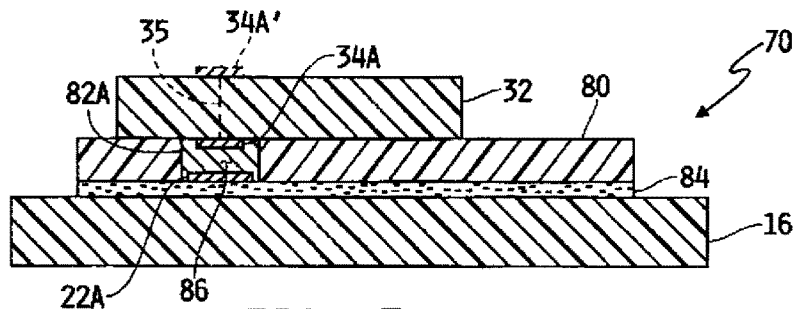
FIG. 7 is a cross-sectional view of the sensor module of FIG. 6 taken along section lines 7-7.
Figure 9:
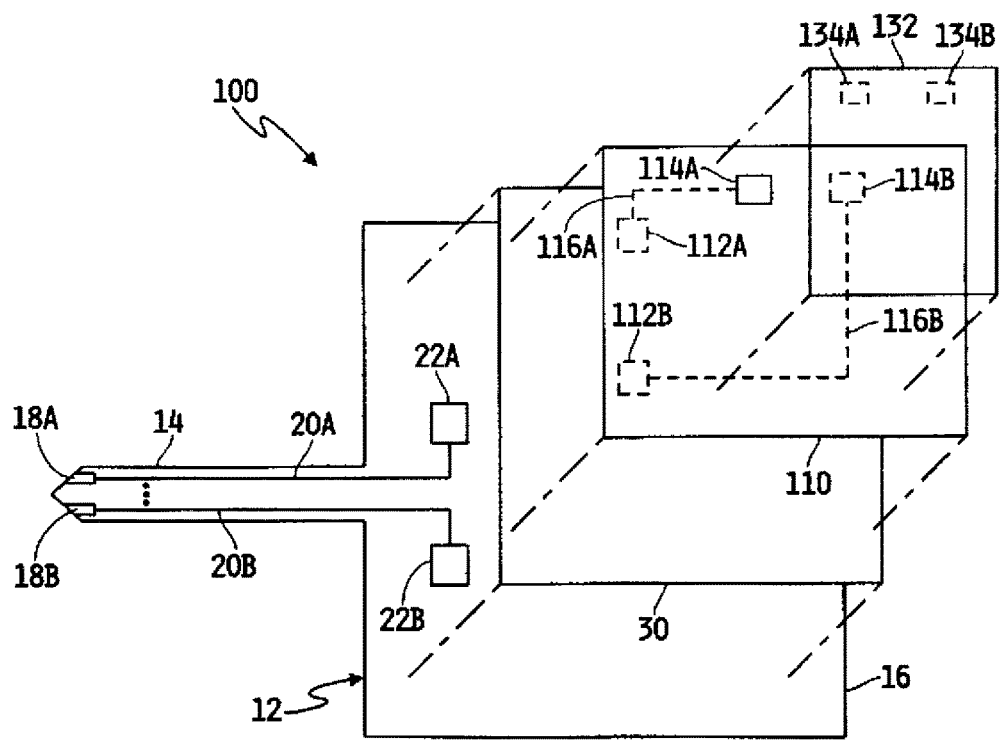
FIG. 9 is an assembly view of yet another embodiment of a sensor module including a sensor and an electrical circuit mountable thereto.
Figure 10:
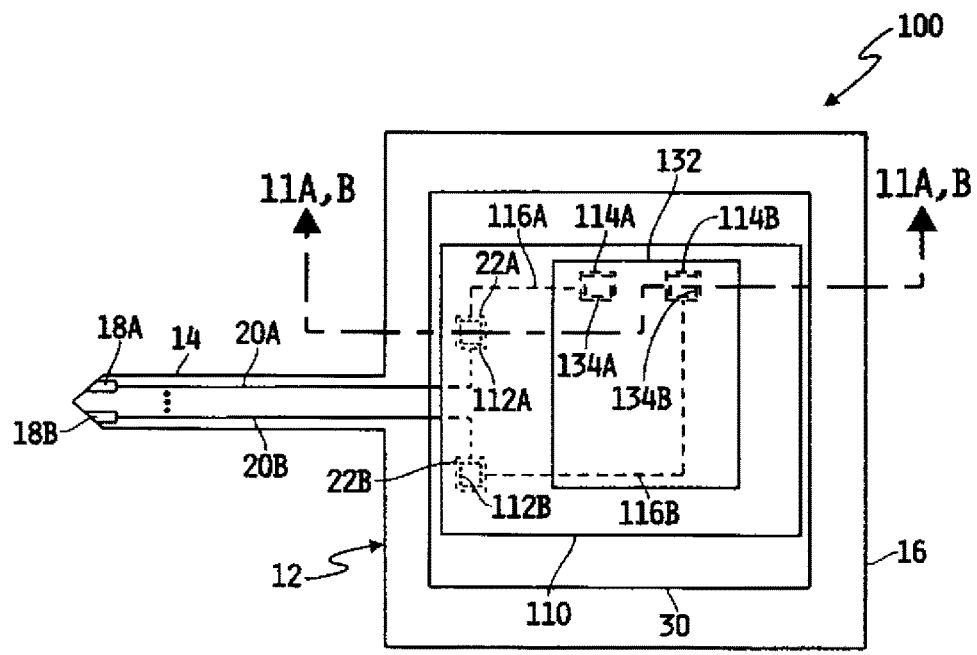
FIG. 10 is an assembled view of the sensor module of FIG. 9.

The one or more electrical terminals defined by the electrical circuit 32 also align with the one or more passageways defined through the intermediate substrate 80. In the illustrated embodiment, for example, the electrical terminals 34A and 34B align with the passageways 82A and 82B respectively so that the terminals 34A and 34B are juxtaposed over the electrically conductive pads 22A and 22B when the electrical circuit 32 is mounted to the intermediate substrate 80 and the intermediate substrate 80 is also mounted to the circuit mounting portion 16 of the substrate 12, as illustrated in FIGS. 6 and 7. Electrical connection between the electrically conductive terminals 34A and 34B and the corresponding electrically conductive pads 22A and 22B respectively is made using conventional electrical interconnection techniques. Examples of such electrical interconnection techniques include, but are not limited to, curable solder paste, solder bumps, electrically conductive adhesive, an electrically conductive formable medium such as an electrically conductive resin, or the like. In the illustrated embodiment, the electrical connection is shown as taking the form of a formable metallic conductor 86, e.g., solder, that forms an electrical and mechanical bond to the electrically conductive terminal 34A and to the electrically conductive pad 22A. This mechanical connection may serve also as the mechanical attachment mechanism for mounting the electrical circuit 32 to the intermediate substrate 80, as illustrated in FIG. 7, or a conventional attachment medium may alternatively be used to attach or mount the electrical circuit 32 to the substrate 80. Examples of such conventional attachment mechanisms include, but are not limited to, conventional epoxies or other formable or settable mediums, conventional adhesives including adhesive tapes, or the like.

The electrical circuit 32 may take any of the forms described hereinabove with respect to FIG. 4, and may be configured as described hereinabove to communicate with a remote electronic device 50. The device 50 may also be configured to communicate with an auxiliary electronic device 62. Details of the remote electronic device 50, the auxiliary electronic device 62 and operation thereof are provided hereinabove. In some embodiments, a portion 32' of the electrical circuit 32 may be mounted to a suitable flexible or rigid substrate 88 that is itself attached to the substrate 80, and a remainder of the electrical circuit 32 may be mounted to and carried by the substrate 80. In the illustrated embodiment, for example, the event notification circuit 46 is shown as being mounted to and carried by the substrate 80 while a remainder 32' of the sensor control circuitry 40, 43, 44 and 48 is mounted to a sensor control circuit substrate 88. It will be understood that in this embodiment, any one or more of the sensor control circuit components may be mounted to the substrate 80, and that the event notification circuit 46 is shown mounted to the substrate 80 only by way of example. In any case, any portion of the sensor control circuit 32 that is mounted to the substrate 80 is electrically connected to a remainder of the sensor control circuit 32' that is mounted to the sensor control circuit substrate 88 using conventional electrical connection structures and techniques. In the illustrated embodiment, for example, the substrate 88 defines an electrically conductive pad or terminal 90 on a top side of thereof that is electrically connected to the sensor operating circuit 40 via an electrically conductive trace 92. The substrate 80 likewise defines an electrically conductive pad or terminal 94 on the top side thereof that is electrically connected to the event notification circuit 46 via an electrically conductive trace 96. The electrically conductive pads or terminals 90 and 94 are electrically connected together in a conventional manner to electrically connect the event notification circuit 46 to the sensor operating circuit 40.

Figure 8:
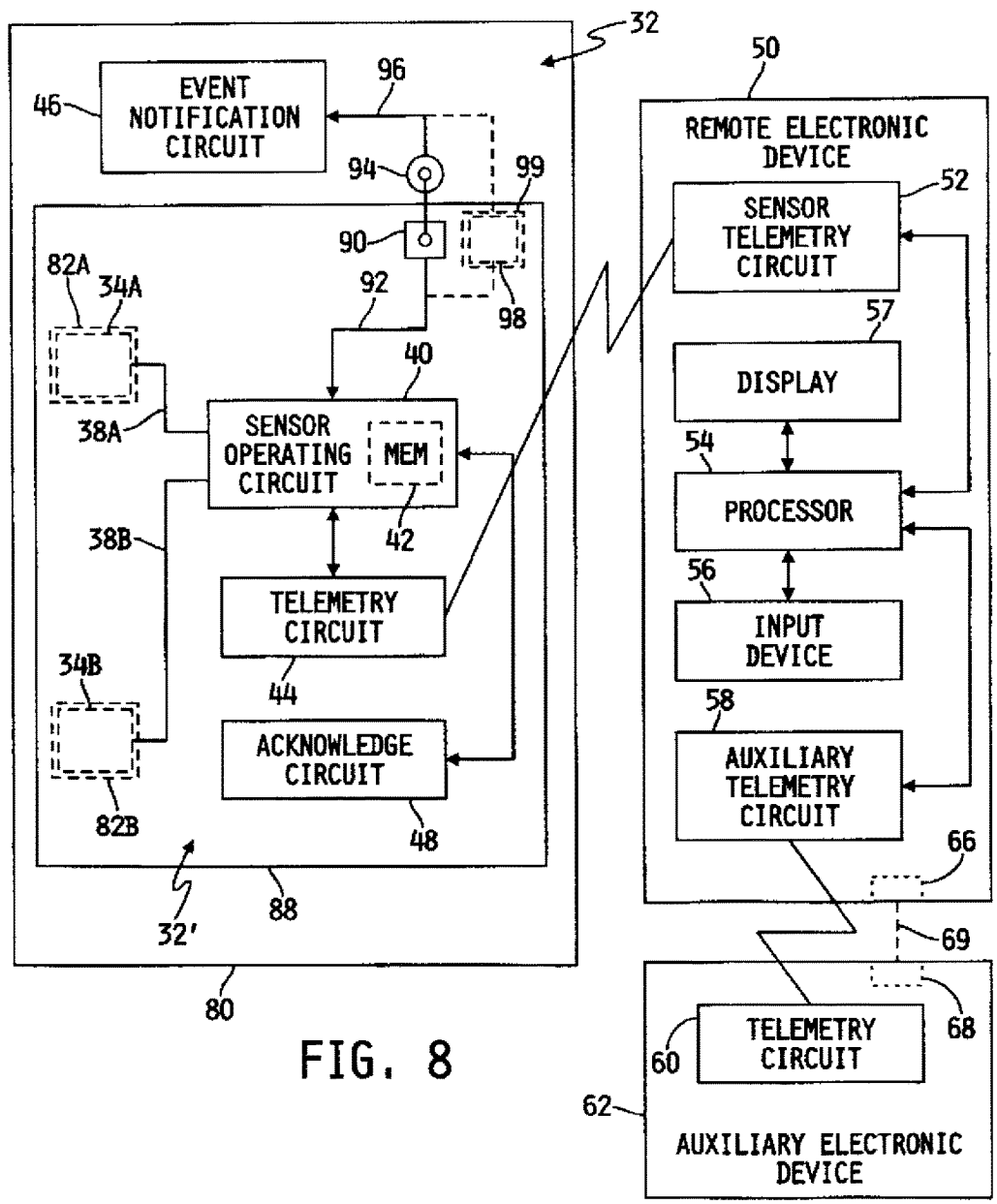
FIG. 8 is a block diagram illustrating one embodiment of the electrical circuit illustrated generally in FIGS. 5 and 6.

In an alternative embodiment, as illustrated in phantom in FIG. 8, the substrate 88 defines an electrically conductive pad 98 on the bottom surface thereof that aligns with, and is juxtaposed over, an electrically conductive pad 99 formed on the top surface of the substrate 80 when the substrate 88 is mounted to the substrate 80. Electrical interconnection therebetween may be made using conventional techniques, or by interposing an anisotropic electrically conductive medium, such as the anisotropic electrically conductive medium 30 illustrated and described hereinabove, between the substrates 80 and 88 at least between the electrically conductive pads 98 and 99. Examples of suitable flexible materials that may be used to implement the substrate 88 in flexible form include, but are not limited to, Melinex® polyester film (e.g., polyethylene terephthalate), other polyesters such as Mylar®, polyvinyl chloride, electrically insulating plastic or polymeric materials such as polycarbonates, polyurethanes, polyethers, polyimides, or copolymers of thermoplastics, such as glycol-modified polyethylene terephthalate, and/or other electrically non-conducting, flexible, deformable materials. Examples of suitable rigid materials that may be used to implement the substrate 88 in rigid form include, but are not limited to, ceramics, such as aluminum oxide and silicon dioxide, conventional printed circuit boards, conventional multi-layer printed circuit boards, and the like. Combinations of flexible and non-flexible materials are also contemplated.

In an alternative embodiment, as another example, the telemetry circuit 44 may be mounted to and carried by the substrate 88 while the remainder 32' of the sensor control circuitry 40, 43, 44 and/or 46 is mounted to and carried by the substrate 80. In this embodiment, the telemetry circuit 44 is electrically connected to a remainder of the sensor control circuit 32' that is mounted to the substrate 80 using conventional electrical connection structures and techniques of the type just described.

Referring now to FIGS. 9-14, one illustrative embodiment of yet another sensor module 100 is shown. The sensor module 100 includes some of the same structural components as the sensor module 10 of FIGS. 1-4, and like numbers are therefore used to identify like components. In the illustrated embodiment, an intermediate substrate 110 is introduced between the circuit mounting portion 16 of the substrate 12 and an electrical circuit 132. The intermediate substrate 110 may be flexible or rigid, and in either case the substrate 110 defines one or more electrically conductive pads on the bottom surface thereof that align with one or more of the number of electrically conductive pads defined on the circuit mounting portion 16 of the substrate 12 when the substrate 110 is mounted to the circuit mounting portion 16 of the substrate 12. In the illustrated embodiment, for example, the intermediate substrate 110 defines two such electrically conductive pads 112A and 112B on the bottom surface thereof that align with corresponding electrically conductive pads 22A and 22B defined on the circuit mounting portion 16 of the substrate 12. In the illustrated embodiment, the substrate 110 is attached to the circuit mounting portion 16 of the substrate 12 via an anisotropic electrically conductive medium 30 as described hereinabove with respect to FIGS. 1-3. In this embodiment, the anisotropic medium 30 also establishes local electrical connections between the electrically conductive pads 22A and 112A and between the electrically conductive pads 22B and 112B as described hereinabove. Alternatively, the substrate 110 may be attached to the circuit mounting portion 16 of the substrate 12 via any conventional attachment medium, and electrical connections between the electrically conductive pads 22A and 112A and between the electrically conductive pads 22B and 112B may be established via any conventional electrical connection structure or technique. Examples of suitable flexible materials that may be used to implement the substrate 110 in flexible form include, but are not limited to, Melinex® polyester film (e.g., polyethylene terephthalate), other polyesters such as Mylar®, polyvinyl chloride, electrically insulating plastic or polymeric materials such as polycarbonates, polyurethanes, polyethers, polyimides, or copolymers of thermoplastics, such as glycol-modified polyethylene terephthalate, and/or other electrically non-conducting, flexible, deformable materials. Examples of suitable rigid materials that may be used to implement the substrate 110 in rigid form include, but are not limited to, ceramics, such as aluminum oxide and silicon dioxide, conventional printed circuit boards, conventional multi-layer printed circuit boards, and the like. Combinations of flexible and non-flexible materials are also contemplated.

The substrate 110 also defines a number of electrically conductive pads on the top surface thereof, at least some of which are electrically connected to corresponding electrically conductive pads defined on the bottom surface of the substrate 110, and one or more of which align with a corresponding one or more electrically conductive pads defined on the bottom surface of the electrical circuit 132 when the electrical circuit 132 is mounted to the substrate 110. In the illustrated embodiment, for example, a pair of electrically conductive pads 114A and 114B are defined on the top surface of the substrate 110. The electrically conductive pad 114A defined on the top surface of the substrate 110 is electrically connected to the electrically conductive pad 112A defined on the bottom surface of the substrate 110 by an electrical conductor or electrically conductive trace 116A, and the electrically conductive pad 114B defined on the top surface of the substrate 110 is likewise electrically connected to the electrically conductive pad 112B defined on the bottom surface of the substrate 110 by an electrical conductor or electrically conductive trace 116B. The electrical conductors or electrically conductive traces 116A and 116B may be formed using conventional electrical connection technology, examples of which include, but are not limited to, plated-though hole technology, using multiple layers of conductors interconnected by vias, wrapping electrically conductive circuit traces around the substrate from the top surface to the bottom surface, and the like.

Figure 11A:
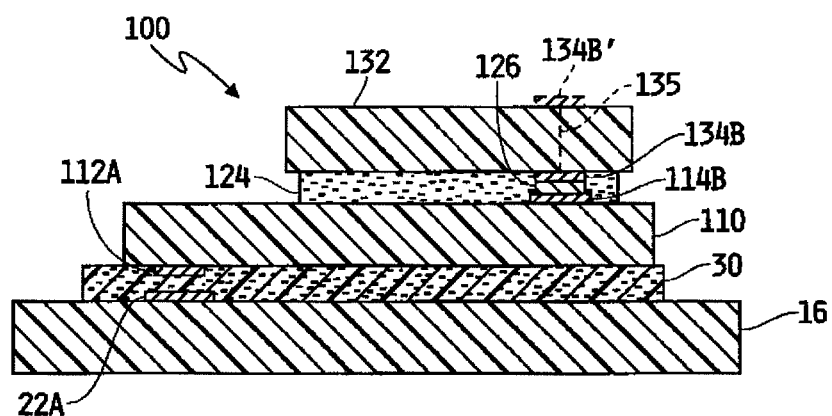
FIG. 11A is a cross-sectional view of one embodiment of the sensor module of FIG. 10 taken along section lines 11A,B-11A,B.
Figure 11B:
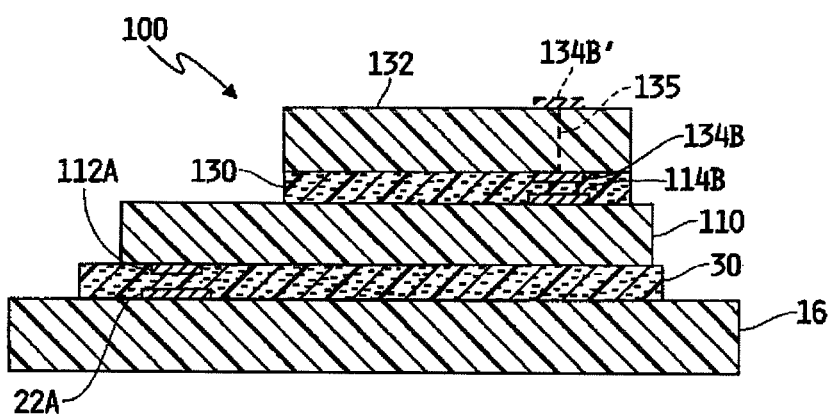
FIG. 11B is a cross-sectional view of another embodiment of the sensor module of FIG. 10 taken along section lines 11A,B-11A,B.

In the illustrated embodiment, the electrical circuit 132 defines a pair of electrically conductive terminals in the form of electrically conductive pads 134A and 134B on the bottom surface thereof, which align with, and are juxtaposed over, corresponding ones of the electrically conductive pads 114A and 114B defined on the top surface of the substrate 110 when the electrical circuit 132 is mounted to the substrate 110. In one embodiment, as illustrated in FIG. 11A, the electrical circuit 132 is attached to the substrate 110 via a conventional attachment medium 124, examples of which include, but are not limited to, conventional epoxies or other formable or settable mediums, conventional adhesives including adhesive tapes, or the like. Electrical connection between the electrically conductive terminals 134A and 134B and the corresponding electrically conductive pads 114A and 114B respectively is made using conventional electrical interconnection techniques. Examples of such electrical interconnection techniques include, but are not limited to, curable solder paste, solder bumps, electrically conductive adhesive, an electrically conductive formable medium such as an electrically conductive resin, or the like. In the illustrated embodiment, the electrical connection is shown as taking the form of a formable metal 126, e.g., solder, that forms an electrical and mechanical bond to the electrically conductive pad 134B and to the electrically conductive pad 114B. In some embodiments, this mechanical connection may serve also as the mechanical attachment mechanism for mounting the electrical circuit 132 to the substrate 110. In an alternate embodiment, as illustrated in FIG. 11B, the electrical circuit 132 is attached to the substrate 110 via an anisotropic electrically conductive medium 130, which may be identical to the anisotropic electrically conductive medium 30 described hereinabove with respect to FIGS. 1-3. In this embodiment, the anisotropic medium 130 also establishes local electrical connections between the electrically conductive pads 134A and 114A and between the electrically conductive pads 134B and 114B as described hereinabove.

The electrical circuit 132 may take any of the forms described hereinabove with respect to the description of the electrical circuit 32, and may be configured as described hereinabove to communicate with a remote electronic device 50. The device 50 may also be configured to communicate with an auxiliary electronic device 62. Details of the remote electronic device 50, the auxiliary electronic device 62 and operation thereof are provided hereinabove.

Figure 12:
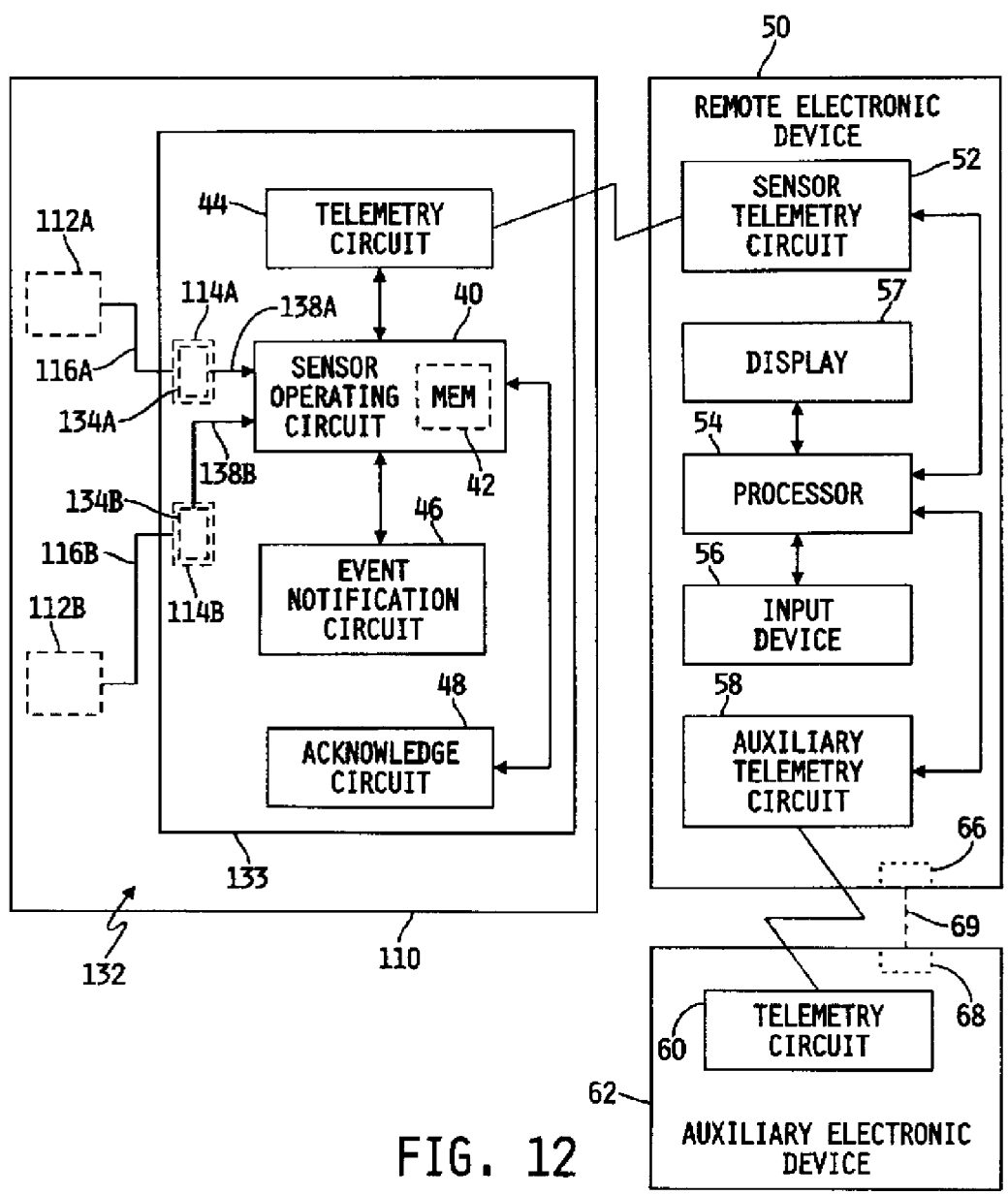
FIG. 12 is a block diagram illustrating one embodiment of the electrical circuit illustrated generally in FIGS. 9, 10, 11A and 11B.

In one embodiment, as illustrated in FIG. 12, for example, the sensor operating circuit 40 is mounted to a top surface of a flexible or rigid substrate 133 that is attached to the substrate 110 as described hereinabove with respect to FIG. 11A or 11B. The sensor operating circuit 40 has a first input that is electrically connected to the electrically conductive pad 134A via an electrical conductor or electrically conductive trace 138A, and a second input that is electrically connected to the electrically conductive pad 134B via an electrical conductor or electrically conductive trace 138B. Optionally, a telemetry circuit 44, an event notification circuit 46 and/or an acknowledge circuit 48 may also be mounted to the substrate 133 and electrically interconnected as described hereinabove. In this embodiment, the sensor operating circuit 40, and optionally any one or more of the telemetry circuit 44, the event notification circuit 46 and the acknowledgement circuit 48, is mounted to a top side of the substrate 133, and the one or more electrical terminals defined on the bottom surface of the substrate 133 are electrically connected to corresponding electrical terminals or circuit traces defined on the top side of the substrate 33 in a conventional manner. This is illustrated in FIGS. 11A and 11B where the electrical terminal 134B defined on the bottom surface of the sensor control circuit 32 is electrically connected via an electrical conductor 135 to an electrical terminal 134B' defined on the top surface of the sensor control circuit 32. The two electrical terminals 134B and 134B' may be electrically connected using conventional techniques including, for example, but not limited to, plated-though hole technology, using multiple layers of conductors interconnected by vias, wrapping electrically conductive circuit traces around the substrate from the top surface to the bottom surface, and the like.

Figure 13:
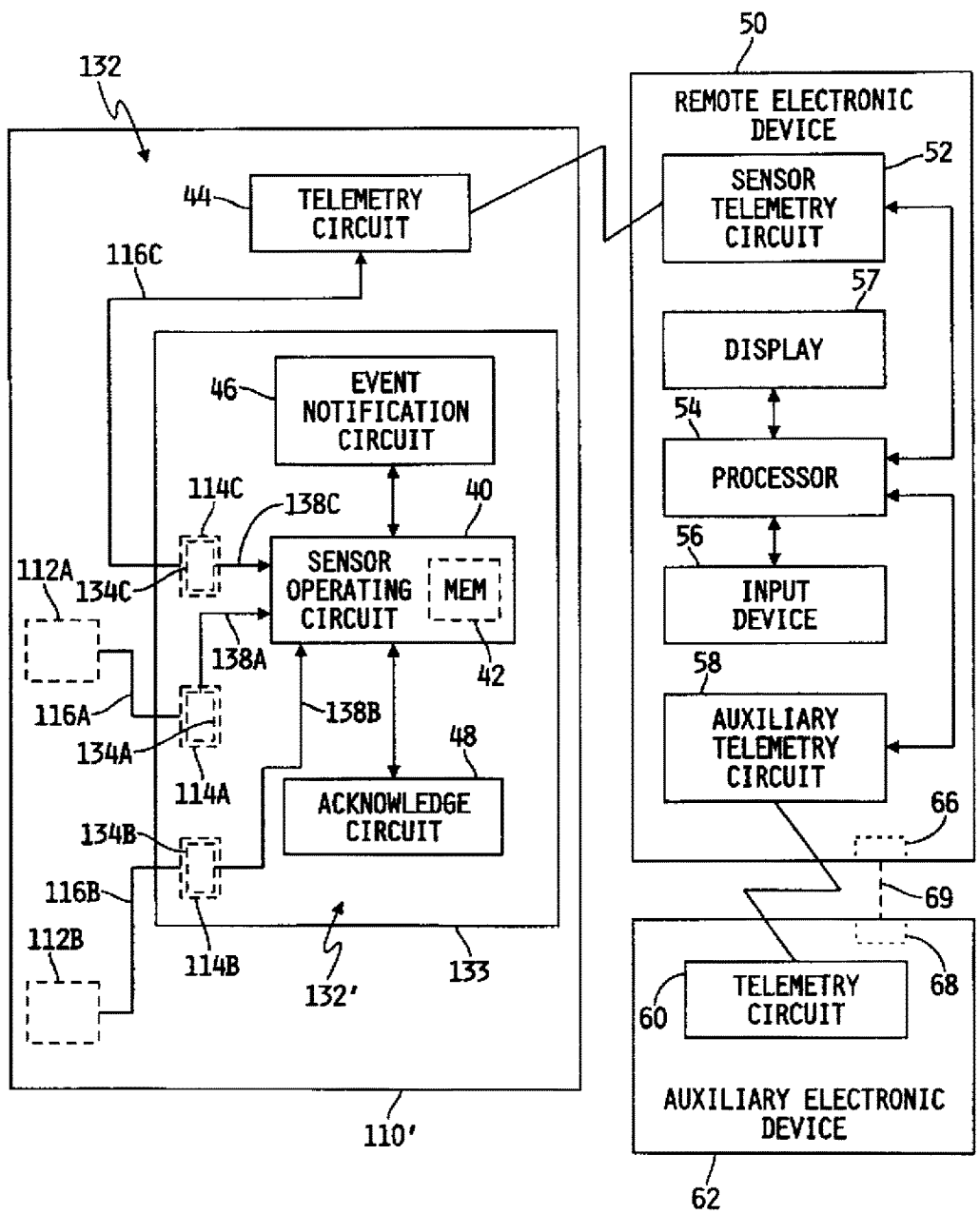
FIG. 13 is a block diagram illustrating another embodiment of the electrical circuit illustrated generally in FIGS. 9, 10, 11A and 11B.

In an alternative embodiment, as illustrated in FIG. 13, for example, a portion 132' of the electrical circuit 132 may be mounted to a modified substrate 133' that is itself attached to a modified substrate 110', and a remainder of the electrical circuit 132 may be mounted to and carried by the substrate 110'. In the illustrated embodiment, for example, the telemetry circuit 44 is shown as being mounted to and carried by the substrate 110' while a remainder 132' of the sensor control circuitry 40, 42, 46 and 48 is mounted to the substrate 133'. It will be understood that in this embodiment, any one or more of the sensor control circuit components may be mounted to the substrate 110', and that the telemetry circuit 44 is shown mounted to the substrate 110' only by way of example. In any case, any portion of the sensor control circuit 132 that is mounted to the substrate 110' is electrically connected to a remainder of the sensor control circuit 132' that is mounted to the substrate 133' using conventional electrical connection structures and techniques. In the illustrated embodiment, for example, the substrate 110' is modified, relative to the substrate 110 of FIG. 12, to define an electrically conductive pad 114C on a top side of thereof that is electrically connected to the telemetry circuit 44 via an electrically conductive trace 116C. The substrate 133' is likewise modified, relative to the substrate 133, to define an electrically conductive pad 134C on the bottom surface thereof that is electrically connected to an input of the sensor operating circuit 40 via an electrically conductive trace 138C. The electrically conductive pads 114C and 134C are electrically connected together as described hereinabove with respect to FIG. 11A or 11B. In the embodiment illustrated in FIG. 13, the electrically conductive pads 112A and 112B defined on the bottom surface of the substrate 110' are shown offset from the center of the substrate 110' to illustrate that the electrically conductive pads may be defined anywhere on the bottom surface of the substrate 110', and this is generally true of any of the electrically conductive pads and/or electrical terminals illustrated and described herein.

Figure 14:
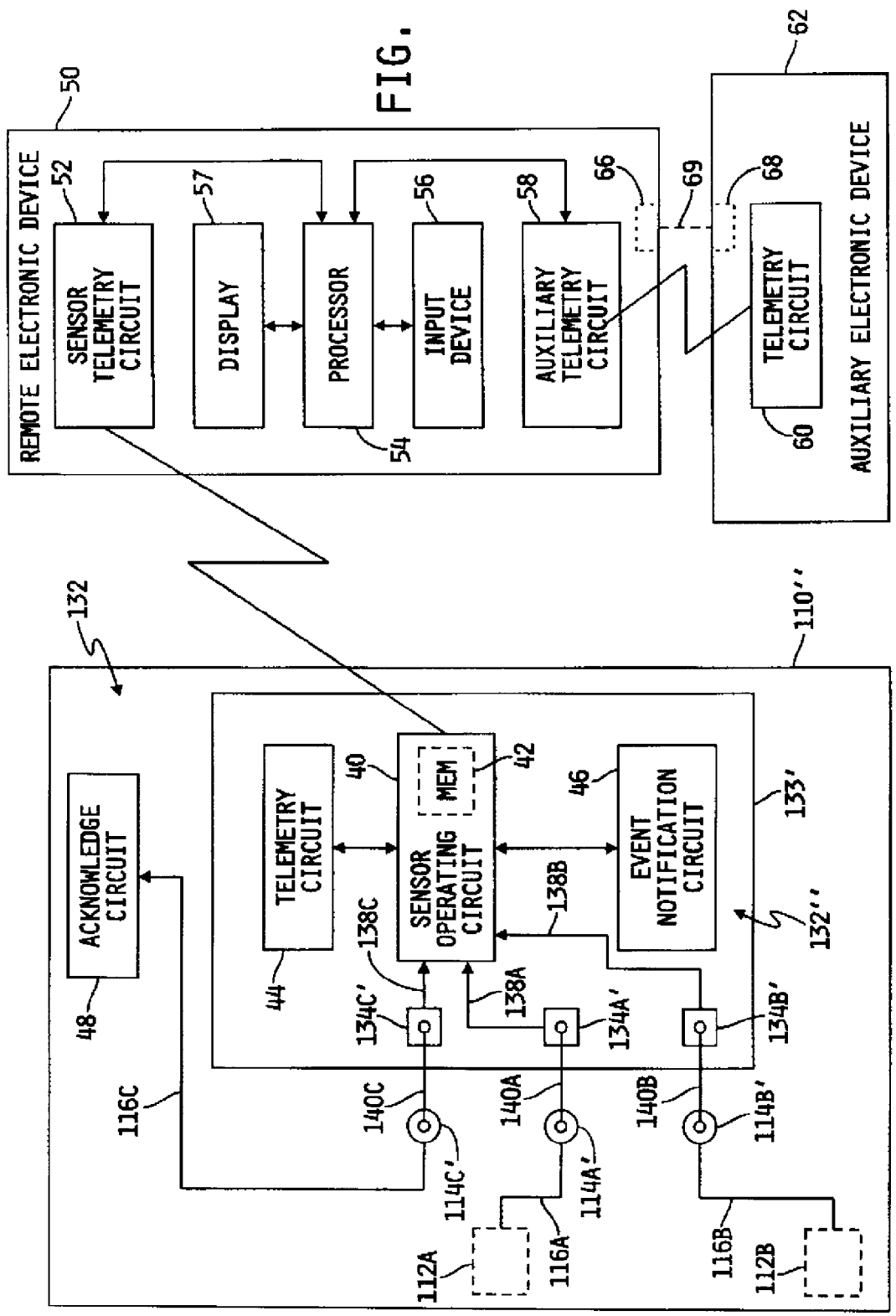
FIG. 14 is a block diagram illustrating yet another embodiment of the electrical circuit illustrated generally in FIGS. 9, 10, 11A and 11B.

In another alternative embodiment, as illustrated in FIG. 14, for example, a portion 132' of the electrical circuit 132 may again be mounted to another modified substrate 133" that is itself attached to another modified substrate 110", and a remainder of the electrical circuit 132 may be mounted to and carried by the substrate 110". In the illustrated embodiment, for example, the acknowledge circuit 48 is shown as being mounted to and carried by the substrate 110" while a remainder 132' of the sensor control circuitry 40, 42, 44 and 48 is mounted to the substrate 133". It will be understood that in this embodiment, any one or more of the sensor control circuit components may be mounted to the substrate 110", and that the acknowledge circuit 48 is shown mounted to the substrate 110" only by way of example.

The substrate 110" is modified, relative to the substrates 110 and 110' of FIGS. 12 and 13 respectively, to define a number of electrically conductive terminals 114A', 114B' and 114C' in place of the electrically conductive pads 114A, 114B and 114C, that may or may not be implemented in the form of electrically conductive pads, that may be defined on the top or bottom surface of the substrate 110" and that may or may not align with corresponding electrical terminals defined on the modified substrate 133". The electrical terminal 114A' is electrically connected to the electrically conductive pad 112A via the circuit trace 116A, the electrical terminal 114B' is electrically connected to the electrically conductive pad 112B via the circuit trace 116B, and the electrical terminal 114C' is electrically connected to the acknowledge circuit 48 via the circuit trace 116C. The substrate 133" is likewise modified to define a number of electrically conductive terminals 134A', 134B' and 134C' in place of the electrically conductive pads 134A, 134B and 134C, that may or may not be implemented in the form of electrically conductive pads, that may be defined on the top or bottom surface of the substrate 133" and that may or may not align with corresponding electrical terminals defined on the modified substrate 110". The electrical terminals 134A', 134B' and 134C' are electrically connected to separate inputs of the sensor operating circuit 40.

In the embodiment illustrated in FIG. 14, the electrical terminals 114A', 114B' and 114C' defined on the substrate 110' are electrically connected to corresponding ones of the electrical terminals 134A', 134B' and 134C' defined on the substrate 133' using electrical connection structures and techniques including, for example, but not limited to, various soldering techniques, clamping techniques and the like. In any of the embodiments illustrated in FIGS. 12-14, examples of suitable flexible materials that may be used to implement the substrates 110, 110', 110", 133, 133' and 133" in flexible form include, but are not limited to, Melinex® polyester film (e.g., polyethylene terephthalate), other polyesters such as Mylar®, polyvinyl chloride, electrically insulating plastic or polymeric materials such as polycarbonates, polyurethanes, polyethers, polyimides, or copolymers of thermoplastics, such as glycol-modified polyethylene terephthalate, and/or other electrically non-conducting, flexible, deformable materials. Examples of suitable rigid materials that may be used to implement the substrates 110, 110', 110", 133, 133' and 133" in rigid form include, but are not limited to, ceramics, such as aluminum oxide and silicon dioxide, conventional printed circuit boards, conventional multi-layer printed circuit boards, and the like. Combinations of flexible and non-flexible materials are also contemplated.

In an alternative embodiment, as another example, the telemetry circuit 44 may be mounted to and carried by the substrate 133 or 133' while the remainder 132' of the sensor control circuitry 40, 43, 44 and/or 46 is mounted to and carried by the substrate 110, 110' or 110". In this embodiment, the telemetry circuit 44 is electrically connected to a remainder of the sensor control circuit 132' that is mounted to the substrate 110, 110' or 110" using conventional electrical connection structures and techniques of the type just described.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. A sensor comprising:
   a first electrically non-conductive substrate having a sensing portion configured to be percutaneously inserted into a patient and an extracorporeal circuit mounting portion, the sensing portion including a sensor having at least one sensor electrode formed thereon in the form of at least a first electrically conductive trace, and the extracorporeal circuit mounting portion having at least one electrically conductive pad formed on one surface thereof, the at least one electrically conductive pad electrically connected to the at least one sensor electrode via at least a second electrically conductive trace formed on the sensing and circuit mounting portions of the first substrate, the sensor configured to produce a signal indicative of a condition of the patient,
   a second substrate having a first surface mounted to the one surface of the first substrate, the first surface of the second substrate defining thereon a first number of electrically conductive pads, the second substrate having a second surface, opposite the first surface, defining thereon a second number of electrically conductive pads, at least one of the first number of electrically conductive pads being aligned with the at least one electrically conductive pad defined on the one surface of the first substrate, the at least one of the first number of electrically conductive pads being electrically connected to at least one of the second number of electrically conductive pads,
   means for establishing electrical contact between the at least one electrically conductive pad defined on the one surface of the first substrate and the at least one of the first number of electrically conductive pads defined on the first surface of the second substrate,
   a third substrate having a first surface mounted to the second surface of the second substrate and defining thereon at least one electrical terminal, the at least one electrical terminal being aligned with the at least one of the second number of electrically conductive pads defined on the second surface of the second substrate,
   a first number of electrical components mounted to a second surface of the third substrate, opposite the first surface thereof, and electrically interconnected to form a sensor control circuit, the sensor control circuit being electrically connected to the at least one electrical terminal defined on the first surface of the third substrate, and
   means for establishing electrical contact between the at least one of the second number of electrically conductive pads defined on the second surface of the second substrate and the at least one electrical terminal defined on the first surface of the third substrate, the sensor being thereby electrically connected to the sensor control circuit.

2. The sensor of claim 1 wherein the sensor control circuit includes a telemetry circuit configured to transmit or receive communication signals to or from a remote electronic device.

3. The sensor of claim 1 wherein the sensor control circuit includes a notification circuit configured to produce any of a visual, audible and tactile indication of a predefined event.

4. The sensor of claim 3 wherein the sensor control circuit includes an acknowledgement circuit responsive to user activation thereof to acknowledge production of the visual, audible or tactile indication of the predefined event.

5. The sensor of claim 3 wherein the sensor control circuit is configured to determine the predefined event from the signal produced by the sensor.

6. The sensor of claim 5 wherein the sensor control circuit further includes a telemetry circuit configured to transmit or receive communication signals to or from a first remote electronic device,
and wherein the first remote electronic device includes a first telemetry circuit configured to transmit or receive communication signals to or from the telemetry circuit of the sensor control circuit.

7. The sensor of claim 6 wherein the telemetry circuit of the sensor control circuit is configured to transmit a signal indicative of the predefined event to the first telemetry circuit of the remote electronic device,
and wherein the first remote electronic device includes means for providing any of a visual, audible and tactile indication of the predefined event.

8. The sensor of claim 6 wherein the first remote electronic device further includes a second telemetry circuit configured to transmit or receive wireless communication signals to or from a second remote electronic device.

9. The sensor of claim 6 further including:
a second remote electronic device, and
means for establishing communications between the first and second remote electronic devices.

10. The sensor of claim 1 wherein the first substrate is a flexible substrate or a rigid substrate.

11. The sensor of claim 1 wherein the second substrate is a flexible substrate or a rigid substrate.

12. The sensor of claim 1 wherein the third substrate is a flexible substrate or a rigid substrate.

13. The sensor of claim 1 further including:
a second number of electrical components mounted to the second surface of the second substrate, the second number of electrical components and the first number of electrical components together forming the sensor control circuit, and
means for electrically connecting the second number of electrical components to the first number of electrical components.

14. The sensor of claim 13 wherein the second number of electrical components includes a sensor operating circuit configured to operate the sensor.

15. The sensor of claim 13 wherein the second number of electrical components includes a telemetry circuit configured to transmit or receive communication signals to or from a remote electronic device.

16. The sensor of claim 13 wherein the second number of electrical components includes a notification circuit configured to produce any of a visual, audible and tactile indication of a predefined event.

17. The sensor of claim 13 wherein the second number of electrical components includes an acknowledgement circuit responsive to user activation thereof to acknowledge production of the visual, audible or tactile indication of the predefined event.

18. The sensor of claim 13 wherein the second number of electrical components includes a sensor operating circuit configured to operate the sensor,
and wherein the first number of electrical components includes a telemetry circuit configured to transmit or receive communication signals to or from a remote electronic device.

19. The sensor of claim 18 wherein the second number of electrical components includes a notification circuit configured to produce any of a visual, audible and tactile indication of a predefined event.

20. The sensor of claim 18 wherein the second number of electrical components includes an acknowledgement circuit responsive to user activation thereof to acknowledge production of the visual, audible or tactile indication of the predefined event.

21. The sensor of claim 1 wherein the first substrate defines a second number of electrically conductive pads on the one surface of the extracorporeal circuit mounting portion thereof,
and wherein at least some of the first number of electrically conductive pads defined on the first surface of the second substrate align with corresponding ones of the second number of electrically conductive pads defined on the one surface of the extracorporeal circuit mounting portion of the first substrate when the first surface of the second substrate is mounted to the one surface of the first substrate.

22. The sensor of claim 21 wherein the first surface of the third substrate defines thereon a number of electrical terminals in addition to the at least one electrical terminal,
and wherein at least others of the second number of electrically conductive pads defined on the second surface of the second substrate align with corresponding ones of the number of electrical terminals defined on the first surface of the third substrate.

23. The sensor of claim 21 wherein the first surface of the third substrate defines thereon a number of electrical terminals in addition to the at least one electrical terminal,
and further including means for electrically connecting at least others of the second number of electrically conductive pads defined on the second surface of the second substrate to corresponding ones of the number of electrical terminals defined on the first surface of the third substrate.

* * * * *